United States Patent
Amid et al.

(10) Patent No.: US 8,870,049 B2
(45) Date of Patent: Oct. 28, 2014

(54) HERNIA STAPLER

(75) Inventors: Parviz K. Amid, Calabasas, CA (US);
Christian Martin, Miami, FL (US);
Scott Arp, Village of Palmetto Bay, FL
(US); Alan Bachman, Milford, CT (US)

(73) Assignee: TransEnterix, Inc., Morrisville, NC (US)

( * ) Notice: Subject to any disclaimer, the term of this patent is extended or adjusted under 35 U.S.C. 154(b) by 0 days.

(21) Appl. No.: 13/425,590

(22) Filed: Mar. 21, 2012

(65) Prior Publication Data
US 2012/0175401 A1 Jul. 12, 2012

Related U.S. Application Data

(63) Continuation-in-part of application No. 12/880,492, filed on Sep. 13, 2010, which is a continuation of application No. PCT/US2009/037119, filed on Mar. 13, 2009.

(60) Provisional application No. 61/036,644, filed on Mar. 14, 2008.

(51) Int. Cl.
*A61B 17/04* (2006.01)
*A61B 17/10* (2006.01)
*A61B 17/068* (2006.01)
*A61B 17/00* (2006.01)
*A61F 2/00* (2006.01)
*A61B 17/064* (2006.01)

(52) U.S. Cl.
CPC ....... *A61B 17/0684* (2013.01); *A61B 17/00234* (2013.01); *A61F 2/0063* (2013.01); *A61B 17/0644* (2013.01)
USPC .................................. 227/176.1; 227/175.1

(58) Field of Classification Search
USPC ............ 227/175.1–182.1; 606/139, 142, 143, 606/219
See application file for complete search history.

(56) References Cited

U.S. PATENT DOCUMENTS 3,638,847 A * 2/1972 Noiles et al. .................. 227/120
3,643,851 A * 2/1972 Green et al. .................... 227/19

(Continued)

FOREIGN PATENT DOCUMENTS

WO    WO 2004/086057 A2    11/2004
WO    WO 2007/030676 A2    3/2007

OTHER PUBLICATIONS

Chapter 14, "Lichtenstein Tension-Free Hernioplasty for the Repair of Primary and Recurrent Inguinal Hernias", Parviz K. Amid, pp. 149-157, of Nyhus and Condon's Hernia, Fifth Edition, edited by Robert J. Fitzgibbons and A. Gerson Greenburg, published by Lippincott Williams & Wilkins, Philadelphia, 2002.

(Continued)

*Primary Examiner* — Robert Long
(74) *Attorney, Agent, or Firm* — Woodard, Emhardt, Moriarty, McNett & Henry LLP

(57) ABSTRACT

A surgical stapler for use during an open hernia repair comprises an elongated shaft having a handle at its proximal end and a downwardly disposed staple discharge head at its distal end. A squeeze trigger on the handle is operable to cause a supply of staples to be selectively discharged from the port. One or more mesh manipulators are provided on the head and serve to assist in positioning or otherwise manipulating surgical mesh prior to fixation with the staples. In one form, the stapler includes a chamfered portion, a cantilevered portion, and a retention lip to prevent multiple staples from deploying after a single pull of the trigger. Further, in this form, the stapler prevents incomplete staple formation if side load forces are applied during insertion of a staple in tissue thereby reducing waste of staples.

15 Claims, 18 Drawing Sheets

(56) References Cited

U.S. PATENT DOCUMENTS

| | | | |
|---|---|---|---|
| 3,650,453 A * | 3/1972 | Smith, Jr. | 227/138 |
| 3,717,294 A * | 2/1973 | Green | 227/19 |
| 3,777,538 A * | 12/1973 | Weatherly et al. | 72/409.01 |
| 3,837,555 A * | 9/1974 | Green | 227/130 |
| 4,014,492 A * | 3/1977 | Rothfuss | 227/19 |
| 4,127,227 A * | 11/1978 | Green | 227/83 |
| 4,242,902 A | 1/1981 | Green | |
| 4,317,451 A | 3/1982 | Cerwin et al. | |
| 4,428,376 A | 1/1984 | Mericle | |
| 4,485,816 A | 12/1984 | Krumme | |
| 4,500,025 A | 2/1985 | Skwor | |
| 4,506,669 A | 3/1985 | Blake, III | |
| 4,523,707 A * | 6/1985 | Blake et al. | 227/19 |
| 4,526,174 A | 7/1985 | Froehlich | |
| 4,527,726 A | 7/1985 | Assell et al. | |
| 4,540,110 A | 9/1985 | Bent et al. | |
| 4,548,202 A | 10/1985 | Duncan | |
| 4,627,437 A * | 12/1986 | Bedi et al. | 606/220 |
| 4,645,111 A * | 2/1987 | Larrabee et al. | 227/19 |
| 4,648,541 A | 3/1987 | Mongeon | |
| 4,655,222 A * | 4/1987 | Florez et al. | 606/219 |
| 4,669,647 A * | 6/1987 | Storace | 227/19 |
| 4,719,917 A | 1/1988 | Barrows et al. | |
| 4,773,420 A | 9/1988 | Green | |
| 4,789,090 A * | 12/1988 | Blake, III | 227/19 |
| 4,991,763 A * | 2/1991 | Storace | 227/177.1 |
| 5,015,249 A | 5/1991 | Nakao et al. | |
| 5,084,057 A * | 1/1992 | Green et al. | 606/142 |
| 5,104,394 A | 4/1992 | Knoepfler | |
| 5,158,567 A | 10/1992 | Green | |
| 5,161,725 A | 11/1992 | Murray et al. | |
| 5,174,487 A | 12/1992 | Rothfuss | |
| 5,192,288 A * | 3/1993 | Thompson et al. | 606/143 |
| 5,217,472 A | 6/1993 | Green et al. | |
| 5,240,164 A | 8/1993 | Murray et al. | |
| 5,246,156 A | 9/1993 | Rothfuss et al. | |
| 5,254,126 A | 10/1993 | Filipi et al. | |
| 5,257,713 A | 11/1993 | Green et al. | |
| 5,281,236 A | 1/1994 | Bagnato et al. | |
| 5,289,963 A * | 3/1994 | McGarry et al. | 227/175.1 |
| 5,290,217 A | 3/1994 | Campos | |
| 5,297,714 A | 3/1994 | Kramer | |
| 5,304,204 A | 4/1994 | Bregen | |
| 5,333,772 A | 8/1994 | Rothfuss et al. | |
| 5,350,400 A | 9/1994 | Esposito et al. | |
| 5,354,312 A * | 10/1994 | Brinkerhoff et al. | 606/207 |
| 5,356,064 A | 10/1994 | Green et al. | |
| 5,364,002 A | 11/1994 | Green | |
| 5,366,479 A | 11/1994 | McGarry et al. | |
| 5,376,097 A | 12/1994 | Phillips | |
| 5,381,943 A | 1/1995 | Allen et al. | |
| 5,389,102 A | 2/1995 | Green et al. | |
| 5,403,326 A | 4/1995 | Harrison et al. | |
| 5,413,272 A | 5/1995 | Green et al. | |
| 5,423,856 A | 6/1995 | Green | |
| 5,456,400 A * | 10/1995 | Shichman et al. | 227/176.1 |
| 5,470,010 A * | 11/1995 | Rothfuss et al. | 227/177.1 |
| 5,484,095 A | 1/1996 | Green et al. | |
| 5,497,933 A | 3/1996 | DeFonzo et al. | |
| 5,501,654 A | 3/1996 | Failla et al. | |
| 5,507,754 A | 4/1996 | Green et al. | |
| 5,527,318 A | 6/1996 | McGarry | |
| 5,536,251 A | 7/1996 | Evard et al. | |
| 5,540,716 A | 7/1996 | Hlavacek | |
| 5,549,637 A | 8/1996 | Crainich | |
| 5,560,532 A | 10/1996 | DeFonzo et al. | |
| 5,562,682 A | 10/1996 | Oberlin et al. | |
| 5,564,615 A | 10/1996 | Bishop et al. | |
| 5,573,541 A | 11/1996 | Green et al. | |
| 5,575,799 A | 11/1996 | Bolanos et al. | |
| 5,577,654 A | 11/1996 | Bishop | |
| 5,588,580 A | 12/1996 | Paul et al. | |
| 5,588,581 A | 12/1996 | Conlon et al. | |
| 5,601,224 A | 2/1997 | Bishop et al. | |
| 5,607,095 A | 3/1997 | Smith et al. | |
| 5,618,311 A | 4/1997 | Gryskiewicz | |
| 5,626,587 A | 5/1997 | Bishop et al. | |
| 5,630,540 A | 5/1997 | Blewett | |
| 5,634,584 A * | 6/1997 | Okorocha et al. | 227/176.1 |
| 5,662,662 A * | 9/1997 | Bishop et al. | 606/143 |
| 5,669,918 A * | 9/1997 | Balazs et al. | 606/139 |
| 5,725,554 A | 3/1998 | Simon et al. | |
| 5,743,456 A | 4/1998 | Jones et al. | |
| 5,766,187 A | 6/1998 | Sugarbaker | |
| 5,797,536 A | 8/1998 | Smith et al. | |
| 5,810,846 A * | 9/1998 | Virnich et al. | 606/142 |
| 5,810,882 A | 9/1998 | Bolduc et al. | |
| 5,817,109 A | 10/1998 | McGarry et al. | |
| 5,829,662 A | 11/1998 | Allen et al. | |
| 5,893,855 A | 4/1999 | Jacobs | |
| 5,908,149 A | 6/1999 | Welch et al. | |
| 5,937,951 A | 8/1999 | Izuchukwu et al. | |
| 5,938,101 A | 8/1999 | Izuchukwu et al. | |
| 6,129,740 A | 10/2000 | Michelson | |
| 6,273,903 B1 | 8/2001 | Wilk | |
| 6,302,311 B1 | 10/2001 | Adams et al. | |
| 6,318,616 B1 * | 11/2001 | Pasqualucci et al. | 227/83 |
| 6,450,391 B1 | 9/2002 | Kayan et al. | |
| 6,511,489 B2 | 1/2003 | Field et al. | |
| 6,533,762 B2 | 3/2003 | Kanner et al. | |
| 6,544,271 B1 | 4/2003 | Adams et al. | |
| 6,582,452 B2 | 6/2003 | Coleman et al. | |
| 6,601,748 B1 | 8/2003 | Fung et al. | |
| 6,609,322 B1 | 8/2003 | Michelson | |
| 6,616,686 B2 * | 9/2003 | Coleman et al. | 606/219 |
| 6,638,297 B1 | 10/2003 | Huitema | |
| 6,652,538 B2 | 11/2003 | Kayan et al. | |
| 6,669,073 B2 | 12/2003 | Milliman et al. | |
| 6,669,714 B2 | 12/2003 | Coleman et al. | |
| 6,679,904 B2 | 1/2004 | Gleeson et al. | |
| 6,685,712 B2 | 2/2004 | Cummins et al. | |
| 6,786,382 B1 | 9/2004 | Hoffman | |
| 6,926,731 B2 * | 8/2005 | Coleman et al. | 606/213 |
| 6,953,139 B2 | 10/2005 | Milliman et al. | |
| 7,004,950 B1 | 2/2006 | Collins et al. | |
| 7,008,435 B2 * | 3/2006 | Cummins | 606/139 |
| 7,014,638 B2 | 3/2006 | Michelson | |
| 7,048,171 B2 | 5/2006 | Thornton et al. | |
| 7,056,330 B2 | 6/2006 | Gayton | |
| 7,059,331 B2 | 6/2006 | Adams et al. | |
| 7,090,684 B2 | 8/2006 | McGuckin, Jr. et al. | |
| 7,111,768 B2 * | 9/2006 | Cummins et al. | 227/175.1 |
| 7,163,551 B2 * | 1/2007 | Anthony et al. | 606/219 |
| 7,213,736 B2 | 5/2007 | Wales et al. | |
| 7,220,237 B2 * | 5/2007 | Gannoe et al. | 604/8 |
| 7,225,964 B2 | 6/2007 | Mastri et al. | |
| 7,229,428 B2 * | 6/2007 | Gannoe et al. | 604/8 |
| RE39,841 E * | 9/2007 | Bilotti et al. | 227/180.1 |
| 7,320,692 B1 * | 1/2008 | Bender et al. | 606/139 |
| 7,401,720 B1 | 7/2008 | Durrani | |
| 7,422,138 B2 * | 9/2008 | Bilotti et al. | 227/179.1 |
| 7,434,716 B2 | 10/2008 | Viola | |
| 7,452,368 B2 | 11/2008 | Liberatore et al. | |
| 7,464,847 B2 | 12/2008 | Viola et al. | |
| 7,473,258 B2 | 1/2009 | Clauson et al. | |
| 7,510,106 B2 * | 3/2009 | Manabe | 227/107 |
| 7,530,484 B1 | 5/2009 | Durrani | |
| 7,530,984 B2 * | 5/2009 | Sonnenschein et al. | 606/139 |
| 7,533,790 B1 | 5/2009 | Knodel et al. | |
| 7,552,853 B2 | 6/2009 | Mas et al. | |
| 7,556,185 B2 | 7/2009 | Viola | |
| 7,556,186 B2 * | 7/2009 | Milliman | 227/182.1 |
| 7,615,058 B2 | 11/2009 | Sixto, Jr. et al. | |
| 7,621,925 B2 | 11/2009 | Saadat et al. | |
| 7,624,903 B2 | 12/2009 | Green et al. | |
| 7,637,905 B2 | 12/2009 | Saadat et al. | |
| 7,651,017 B2 * | 1/2010 | Ortiz et al. | 227/176.1 |
| 7,708,181 B2 | 5/2010 | Cole et al. | |
| 7,736,374 B2 | 6/2010 | Vaughan et al. | |
| 7,744,613 B2 | 6/2010 | Ewers et al. | |
| 7,766,208 B2 * | 8/2010 | Epperly et al. | 227/175.1 |
| 7,771,440 B2 | 8/2010 | Ortiz et al. | |
| 7,776,057 B2 | 8/2010 | Laufer et al. | |
| 7,794,474 B2 | 9/2010 | Michler et al. | |

(56) References Cited

U.S. PATENT DOCUMENTS

| | | | |
|---|---|---|---|
| 7,857,187 B2 * | 12/2010 | Milliman | 227/179.1 |
| 7,866,526 B2 | 1/2011 | Green et al. | |
| 7,914,543 B2 | 3/2011 | Roth et al. | |
| 7,942,884 B2 | 5/2011 | Vahid et al. | |
| 7,954,688 B2 | 6/2011 | Argentine et al. | |
| 7,997,468 B2 | 8/2011 | Farascioni | |
| 8,011,553 B2 | 9/2011 | Mastri et al. | |
| 8,011,555 B2 * | 9/2011 | Tarinelli et al. | 227/180.1 |
| 8,056,788 B2 | 11/2011 | Mastri et al. | |
| 8,066,720 B2 | 11/2011 | Knodel et al. | |
| 8,123,101 B2 | 2/2012 | Racenet et al. | |
| 8,136,711 B2 | 3/2012 | Beardsley et al. | |
| 8,186,556 B2 * | 5/2012 | Viola | 227/178.1 |
| 8,231,041 B2 * | 7/2012 | Marczyk et al. | 227/178.1 |
| 8,252,009 B2 | 8/2012 | Weller et al. | |
| 8,393,516 B2 * | 3/2013 | Kostrzewski | 227/180.1 |
| 8,469,972 B2 | 6/2013 | Harris et al. | |
| 8,500,777 B2 | 8/2013 | Harris et al. | |
| 2002/0049472 A1 | 4/2002 | Coleman et al. | |
| 2002/0065535 A1 | 5/2002 | Kneifel et al. | |
| 2002/0077660 A1 | 6/2002 | Kayan et al. | |
| 2002/0117534 A1 | 8/2002 | Green et al. | |
| 2003/0199924 A1 | 10/2003 | Coleman et al. | |
| 2003/0222118 A1 | 12/2003 | Brown | |
| 2004/0006372 A1 | 1/2004 | Racenet et al. | |
| 2004/0044364 A1 | 3/2004 | DeVries et al. | |
| 2004/0073237 A1 | 4/2004 | Leinsing | |
| 2004/0073257 A1 | 4/2004 | Spitz | |
| 2004/0138525 A1 | 7/2004 | Saadat et al. | |
| 2004/0138705 A1 | 7/2004 | Heino et al. | |
| 2004/0173659 A1 | 9/2004 | Green et al. | |
| 2004/0230208 A1 | 11/2004 | Shayani | |
| 2004/0243151 A1 | 12/2004 | Demmy et al. | |
| 2004/0267310 A1 | 12/2004 | Racenet et al. | |
| 2005/0051597 A1 | 3/2005 | Toledano | |
| 2005/0080434 A1 | 4/2005 | Chung et al. | |
| 2005/0159777 A1 | 7/2005 | Spitz | |
| 2005/0216057 A1 | 9/2005 | Coleman et al. | |
| 2005/0256537 A1 | 11/2005 | Cummins et al. | |
| 2005/0267530 A1 | 12/2005 | Cummins | |
| 2006/0097026 A1 | 5/2006 | Shelton, IV | |
| 2007/0043384 A1 | 2/2007 | Ortiz et al. | |
| 2007/0080188 A1 | 4/2007 | Spence et al. | |
| 2007/0114261 A1 * | 5/2007 | Ortiz et al. | 227/175.1 |
| 2007/0213585 A1 | 9/2007 | Monassevitch et al. | |
| 2007/0282356 A1 * | 12/2007 | Sonnenschein et al. | 606/153 |
| 2008/0000941 A1 * | 1/2008 | Sonnenschein et al. | 227/120 |
| 2008/0065153 A1 | 3/2008 | Allard et al. | |
| 2008/0065154 A1 | 3/2008 | Allard et al. | |
| 2008/0135600 A1 * | 6/2008 | Hiranuma et al. | 227/176.1 |
| 2008/0173691 A1 * | 7/2008 | Mas et al. | 227/175.1 |
| 2008/0217376 A1 | 9/2008 | Clauson et al. | |
| 2008/0243143 A1 | 10/2008 | Kuhns et al. | |
| 2008/0249565 A1 | 10/2008 | Michler et al. | |
| 2008/0269801 A1 | 10/2008 | Coleman et al. | |
| 2008/0272173 A1 * | 11/2008 | Coleman et al. | 227/175.1 |
| 2009/0069806 A1 | 3/2009 | De La Mora Levy et al. | |
| 2009/0105535 A1 * | 4/2009 | Green et al. | 600/106 |
| 2009/0134198 A1 * | 5/2009 | Knodel et al. | 227/176.1 |
| 2009/0242609 A1 * | 10/2009 | Kanner | 227/175.1 |
| 2009/0277949 A1 * | 11/2009 | Viola et al. | 227/178.1 |
| 2009/0308908 A1 | 12/2009 | Green et al. | |
| 2009/0314820 A1 * | 12/2009 | Green et al. | 227/176.1 |
| 2009/0318936 A1 | 12/2009 | Harris et al. | |
| 2010/0012704 A1 * | 1/2010 | Tarinelli Racenet et al. | 227/180.1 |
| 2010/0094315 A1 | 4/2010 | Beardsley et al. | |
| 2010/0187285 A1 * | 7/2010 | Harris et al. | 227/179.1 |
| 2010/0191255 A1 * | 7/2010 | Crainich et al. | 606/142 |
| 2010/0320252 A1 * | 12/2010 | Viola et al. | 227/176.1 |
| 2010/0327042 A1 | 12/2010 | Amid et al. | |
| 2011/0049213 A1 * | 3/2011 | Schneider et al. | 227/120 |
| 2011/0168756 A1 | 7/2011 | Racenet et al. | |
| 2011/0168758 A1 | 7/2011 | Mastri et al. | |
| 2011/0218550 A1 | 9/2011 | Ma | |
| 2011/0297730 A1 | 12/2011 | Mastri et al. | |
| 2011/0315740 A1 | 12/2011 | Stopek | |
| 2012/0104073 A1 * | 5/2012 | Milliman et al. | 227/181.1 |
| 2012/0160893 A1 | 6/2012 | Harris et al. | |
| 2012/0193391 A1 | 8/2012 | Michler et al. | |
| 2012/0234898 A1 * | 9/2012 | Shelton et al. | 227/179.1 |
| 2013/0306704 A1 | 11/2013 | Balbierz et al. | |

OTHER PUBLICATIONS

Chapter 23, "The Transabdominal Preperitoneal Laparoscopic Herniorrhaphy", Fitzgibbons & Filipi, pp. 256-268 of Nyhus and Condon's Hernia, Fifth Edition, edited by Robert J. Fitzgibbons and A. Gerson Greenburg, published by Lippincott Williams & Wilkins, Philadelphia, 2002.
China Application No. 200980108633.1 English Translation of Office Action mailed Feb. 13, 2012.
International Patent Application No. PCT/US2009/037119 International Preliminary Report on Patentability mailed Sep. 23, 2010.
Singapore Application No. 201006248-7 Written Opinion mailed Sep. 9, 2011.
U.S. Appl. No. 12/880,492 to Amid et al., Office Action mailed Aug. 4, 2011.
U.S. Appl. No. 12/880,492 to Amid et al., Office Action mailed Mar. 16, 2011.
International Patent Application No. PCT/US2009/037119 Search Report mailed Oct. 28, 2009.
International Patent Application No. PCT/US2009/037119 Written Opinion mailed Oct. 28, 2009.
Japan Application No. 2010-550893, Notice of Reasons for Rejection mailed Jun. 11, 2013.
U.S. Appl. No. 12/880,492 to Amid et al., Final Office Action mailed May 23, 2013.
U.S. Appl. No. 12/880,492 to Amid et al., Office Action mailed Apr. 24, 2012.
U.S. Appl. No. 12/880,492 to Amid et al., Office Action mailed Oct. 18, 2012.
U.S. Appl. No. 12/880,492 to Amid et al., Final Office Action mailed Feb. 12, 2014.
U.S. Appl. No. 12/880,492 to Amid et al., Notice of Allowance mailed May 9, 2014.

* cited by examiner

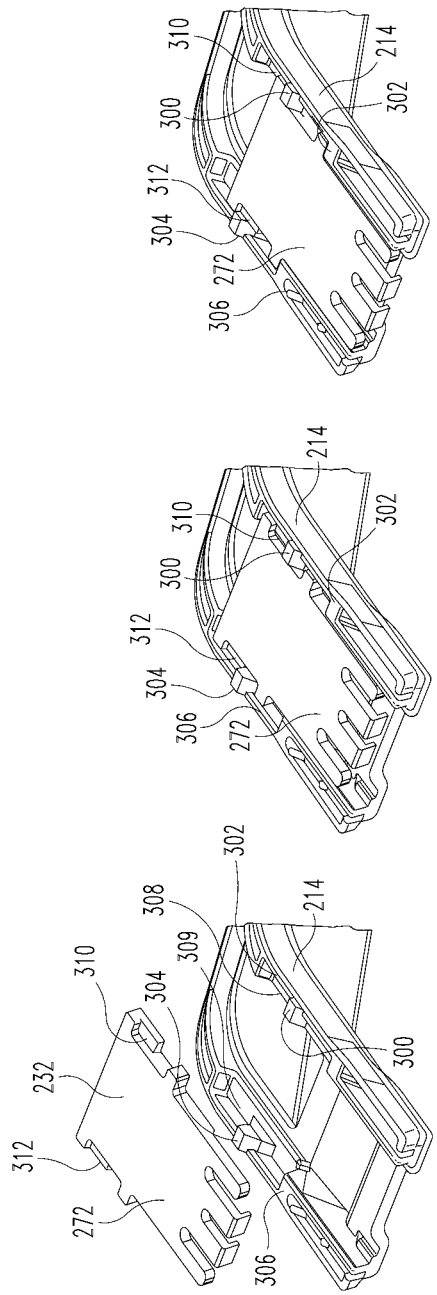

HERNIA STAPLER

CROSS-REFERENCE TO RELATED APPLICATION

This application is a continuation-in-part of U.S. patent application Ser. No. 12/880,492 filed Sep. 13, 2010, which is a continuation of PCT/US2009/037119 filed Mar. 13, 2009, which claims the benefit of U.S. Provisional Application Ser. No. 61/036,644 filed Mar. 14, 2008, the disclosures of which are hereby incorporated by reference.

BACKGROUND

This application is generally related to means for applying surgical staples to fasten a surgical mesh. More specifically, but not exclusively, it is related to a surgical stapler having a distal manipulator for positioning a surgical mesh prior to application of the staples.

Chapters 14 and 23 of "Lichtenstein Tension-Free Hernioplasty For The Repair of Primary and Recurrent Inguinal Hernias", pages 149-157 of "The Transabdominal Preperitoneal Laparoscopic Herniorrhaphy", and pages 256-268 of *Nyhus and Condon's Hernia, Fifth Edition*, edited by Robert J. Fitzgibbons and A. Gerson Greenburg, published by Lippincott Williams & Wilkins, Philadelphia, 2002, describe some procedures for repair of inguinal hernias. A sheet of monofilamented polypropylene mesh is mentioned as a material suitable for use in such procedures. After shaping and placement of the mesh in the repair site, it is sutured to adjacent tissue.

While suturing is a long-standing practice for securing the mesh, some stapling is frequently favored because of the speed and relative ease of use. At some locations desired for attachment of the mesh to tissue, stapling is possible, but holding and stapling the mesh to tissue at some other locations where attachment is desired can be challenging, if not impossible, for one pair of hands. Improvement is needed.

SUMMARY

The present invention provides systems and techniques for applying surgical staples and for using staples to hold a surgical mesh, for example during an inguinal hernia repair. The systems and techniques may also be applied during ventral/incisional hernia repair, used for skin closure, or used in other surgical procedures as would occur to the skilled artisan. While the actual nature of the invention covered herein can only be determined with reference to the claims appended hereto, certain aspects of the invention that are characteristic of the embodiments disclosed herein are described briefly as follows.

According to one aspect, a surgical stapler includes an elongated shaft having a handle at its proximal end and a downwardly disposed discharge head at its distal end. The stapler also includes an angled magazine of staples mounted between the discharge head and the shaft and a pusher plate disposed in the discharge head. In one form, the pusher plate includes a pair of forming fingers adapted to retain a single staple from the magazine of staples between the forming fingers. Moreover, in another form, each of the pair of forming fingers includes a retention lip. Typically, the retention lip has a height that corresponds to a thickness of the single staple. In yet another form, each of the pair of forming fingers includes an inner edge, an outer edge, and a staple contact portion that spans between the inner and outer edges, wherein the inner edge and the staple contact portion include a retention lip. Each of the pair of forming fingers may also include a chamfered portion adapted to engage only the single staple from the magazine of staples. Some embodiments include an anvil plate positioned in the discharge head adjacent the pusher plate wherein the anvil plate has a step with a height that corresponds to about the thickness of the single staple and the step is adapted to position the single staple under the chamfered portion when the pusher plate passes over the anvil plate. The pair of forming fingers can be adapted to slide adjacent the step.

According to another aspect, a novel surgical stapler includes an elongated shaft having a handle at its proximal end and a downwardly disposed staple discharge head at its distal end, wherein the handle is operable to cause a supply of staples to be selectively discharged from the head. The stapler includes a pusher plate positioned in the staple discharge head wherein the pusher plate includes a retention lip adapted to retain a single staple from the supply of staples during a hernia surgery. In some forms, the pusher plate includes a chamfered portion adapted to engage only the single staple from the magazine of staples. In other forms, the pusher plate includes a cantilevered portion adapted to engage and remove the single staple from the supply of staples. The stapler can include an anvil plate positioned in the discharge head adjacent the pusher plate wherein the anvil plate has a step with a height that corresponds to about the thickness of the single staple and the step is adapted to position the single staple under the chamfered portion when the pusher plate passes over the anvil plate. Further, in one form, the elongated shaft includes a first tab and a second tab, the anvil plate defines a first keyway and a second keyway, and the first and second tabs are adapted to engage and retain the first and second keyways, respectively, when the anvil plate is assembled with the elongated shaft.

Further forms, objects, features, aspects, benefits, advantages, and embodiments of the present invention will become apparent from a detailed description and drawings provided herewith.

BRIEF DESCRIPTION OF THE DRAWINGS

FIG. 1A is an enlarged fragmentary view of a portion of the stapler head showing a staple projecting from the staple exit port and showing the tip of a mesh positioning probe wire.

FIG. 22 is a top view of the backwall and base from FIG. 15 embodiment.

FIG. 23 is a partially assembled view of the FIG. 22 embodiment.

FIG. 24 is a fully assembled view of the FIG. 22 embodiment.

DESCRIPTION OF THE SELECTED EMBODIMENTS

Figure 1:
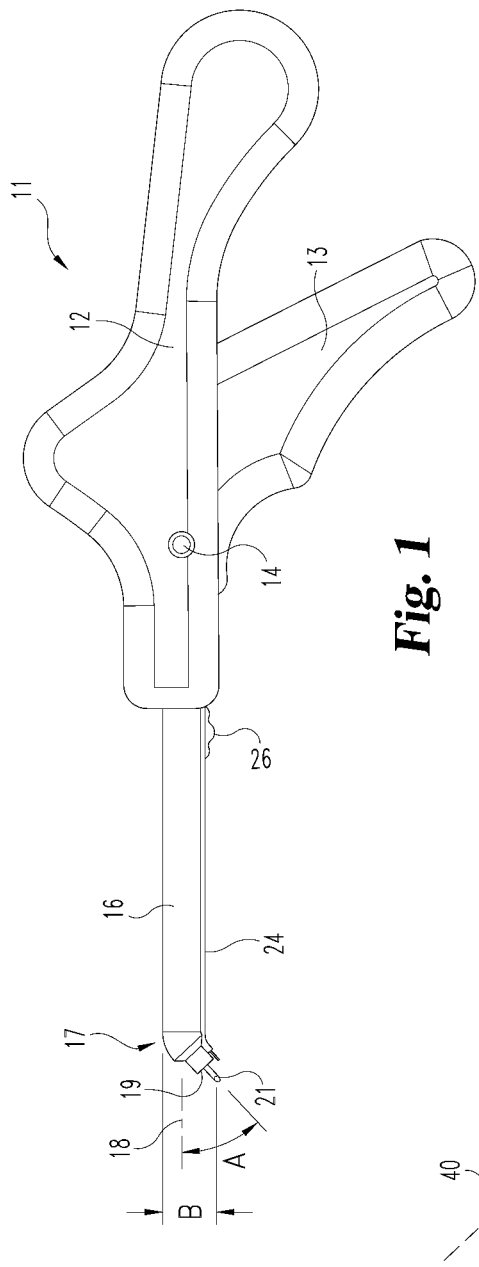
FIG. 1 is a side elevational view of an embodiment of the present invention.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail, although it will be apparent to those skilled in the relevant art that some features that are not relevant to the present invention may not be shown for the sake of clarity.

Figures 2, 2A:
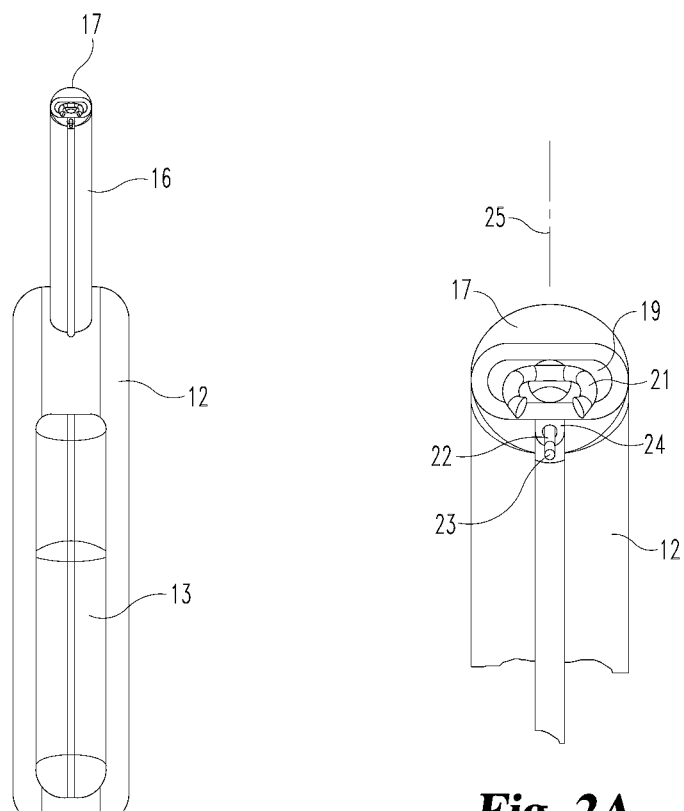
FIG. 2 is a front elevational view of the stapler.
FIG. 2A is an enlarged fragmentary front view of the stapler head portion.

Referring to FIGS. 1-2A, a stapler 11 has a handle 12 with a trigger 13 pivotally mounted to the handle at 14. A shaft or tube 16 is fixed to the handle and has a stapler head portion 17 at its distal end. The head portion turns downward at an angle of about forty degrees (A in FIG. 1) from an axis 18 and has a staple discharge port 19 through which staples are shot, one staple for each trigger pull. The trigger coupling to the staple shooter is a two-stage system whereby a staple 21 can be advanced from within the head to a position shown in FIGS. 1 and 1A. Then, upon further pull of the trigger it can be shot through the mesh into the tissue.

One inventive feature is the provision of a mesh manipulator near the outlet port of the stapler. As used herein, a "mesh manipulator" does not include the staple itself, but rather it is a structure other than the staple that is operable to be used to manipulate surgical mesh. In FIGS. 1 and 1A, the mesh manipulator comprises an elongated member or wire 22 having a distal portion including a tip 23 which projects downward under the stapler head portion 17 in the plane 25 (FIG. 2A) containing the axis 18 of the tube 16 and bisecting the handle 12. This elongated member extends from the tip portion backward through a channel 24 at the bottom of the tube 16. A wire control button 26 slidable on the channel and connected to the proximal end of the wire is provided to slide the wire forward to extend the tip 23 farther below the staple discharge port 19, or retract it into the channel 24 when and to what extent desired by the surgeon. Other locations for the wire control button 26 can be used when and desired by the user. One example is in the handle itself.

For purposes of useful mesh manipulation, the wire 22 would often, but not always, be positioned such that the tip 23 projects several millimeters beyond the plane 40 defined by the discharge port 19, as shown in FIG. 1A. For example, it is expected that useful mesh manipulation can be achieved when the tip 23 is at least about 2 mm, 3 mm, 4 mm, 5 mm, 6 mm, 7 mm, 8 mm, 9 mm, or 10 mm distal to plane 40.

Figure 3:
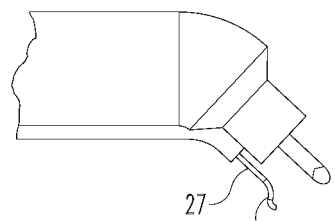
FIG. 3 is an enlarged fragmentary schematic view of the stapler head portion with a probe wire type curved forward to push mesh to a desired position on body tissue for stapling.
Figure 3A:
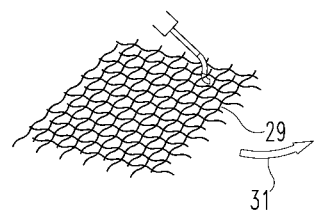
FIG. 3A illustrates the actual use of the wire pushing a piece of mesh forward.

Referring now to FIGS. 3 and 3A, a wire 27 is provided with a curved tip portion 28 curved downward and forward for insertion through a mesh 29 and pushing it forward in the direction of arrow 31 to move it to the position desired for stapling. This forward movement may be made by moving the stapler itself using the handle or by moving the wire by moving the wire control button 26.

Figure 4:
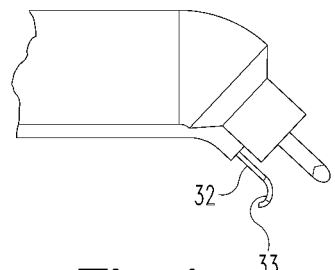
FIG. 4 is a view similar to FIG. 3 but showing the probe wire tip portion angled backward to pull the mesh.
Figure 4A:
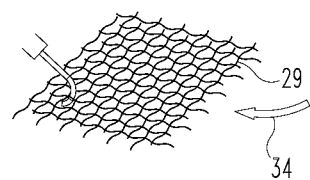
FIG. 4A is similar to FIG. 3A but showing the tip of FIG. 4 engaged to pull the mesh.

Referring to FIGS. 4 and 4A, a wire 32 has a tip portion 33 which is curved rearward to enable the wire tip to pass through the mesh 29 and pull it rearward in the direction of arrow 34 to position the mesh where desired relative to the location at which the stapling through the mesh to the tissue is desired.

Figure 5:
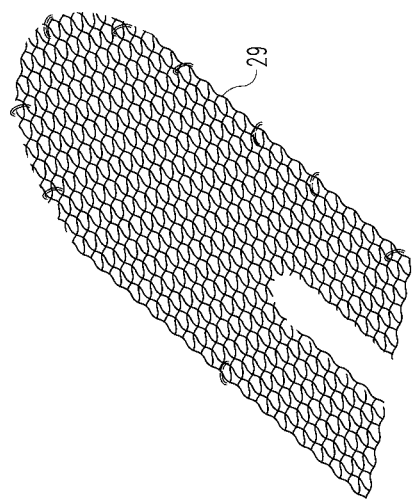
FIG. 5 is a schematic view of a piece of mesh shaped for placement in the repair site and illustrating the location where stapling is desired.

Referring now to FIG. 5, there is a schematic showing the mesh 29 cut from a sheet into a shape desired for placement at the surgery site. There are shown eleven sites at the edges of the mesh indicating where stapling inboard from the edges is desired. This is an example, as different sizes and shapes and numbers of staples may be chosen depending upon the requirements of the site.

Figure 6:
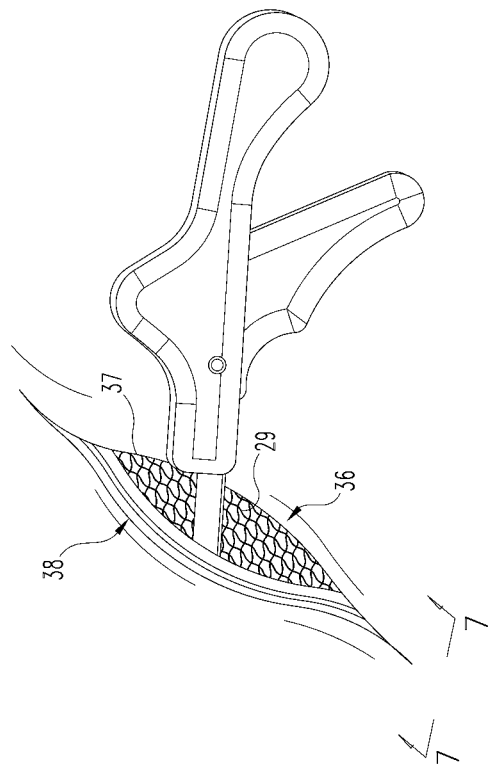
FIG. 6 is a schematic view of the repair site with stapler head in the opening.
Figure 7:
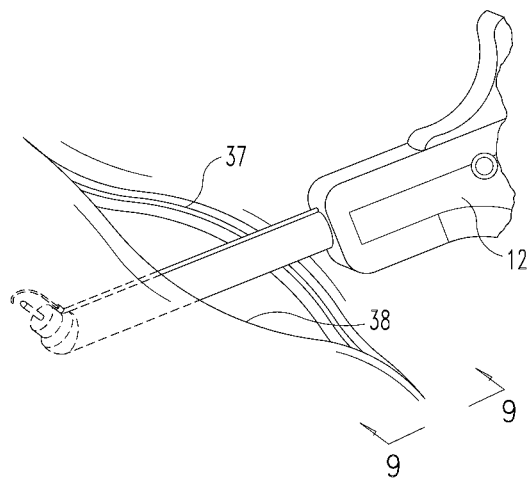
FIG. 7 is a schematic view of the repair site with the stapler in position for stapling the mesh to the underside of body tissue at the far side of the opening.
Figure 8A:
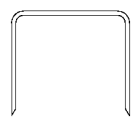
FIG. 8A is a view of a staple before installation.
Figure 8B:
FIGS. 8B, 8C, 8D and 8E represent four possible different configurations of the staple after stapling, the shapes being determined by staple forming features specified for incorporation in the stapler head.
Figure 8C:
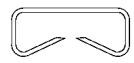
Figure 8D:
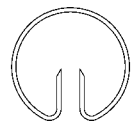
Figure 8E:
Figure 9:
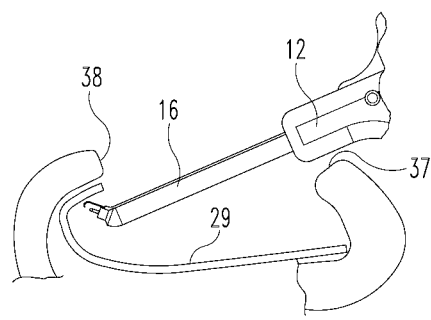
FIG. 9 is a schematic of the site and viewed in the direction of arrows 9-9 in FIG. 7.

FIG. 6 is a schematic illustration of the site with the staple head inserted into an opening 36. Consider that an opening edge 37 nearest the surgeon is referred to in this context, as the near edge, and an opposite edge 38 is the far edge. Attachment of the mesh to tissue below the near edge 37 by stapling can be relatively straight forward with the stapler oriented as shown in FIG. 6, but pulled outward to place the head at the near edge 37 and move the head downward to the mesh and shoot the staple down into the mesh with the prongs into the tissue below. On the opposite edge, the mesh is to be stapled to the upper inside face of the tissue. That is extremely difficult with conventional instruments. The present invention is capable of being turned upside down as shown in FIGS. 7 and 9 so that the discharge port 19 and tip 23 are facing upwardly to the tissue and pushed or pulled by a wire tip such as shown in FIG. 3 or FIG. 4, depending upon the most effective approach to push or pull the mesh to the location desired for stapling and then fire the staple upward with the prongs through the mesh and into inverted or lofted tissue.

In FIG. 1, for example and without limitation, the stapler head portion 17 has the discharge port angled down as shown at A. As an example, this angle can be between 30 and 50 degrees from the center line 18 of the shaft. In one example, 45 degrees might be the optimal angle.

Figure 10:
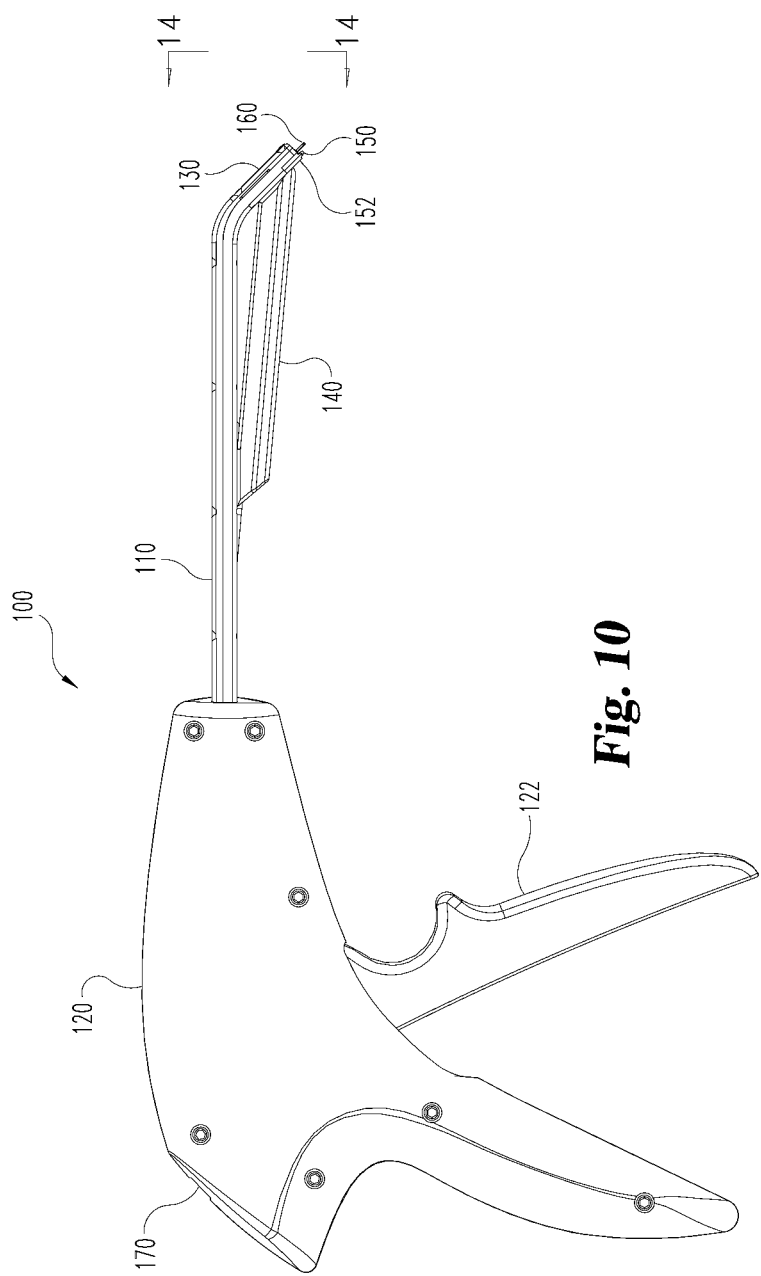
FIG. 10 is a side elevational view of a stapler of new construction.
Figure 11:
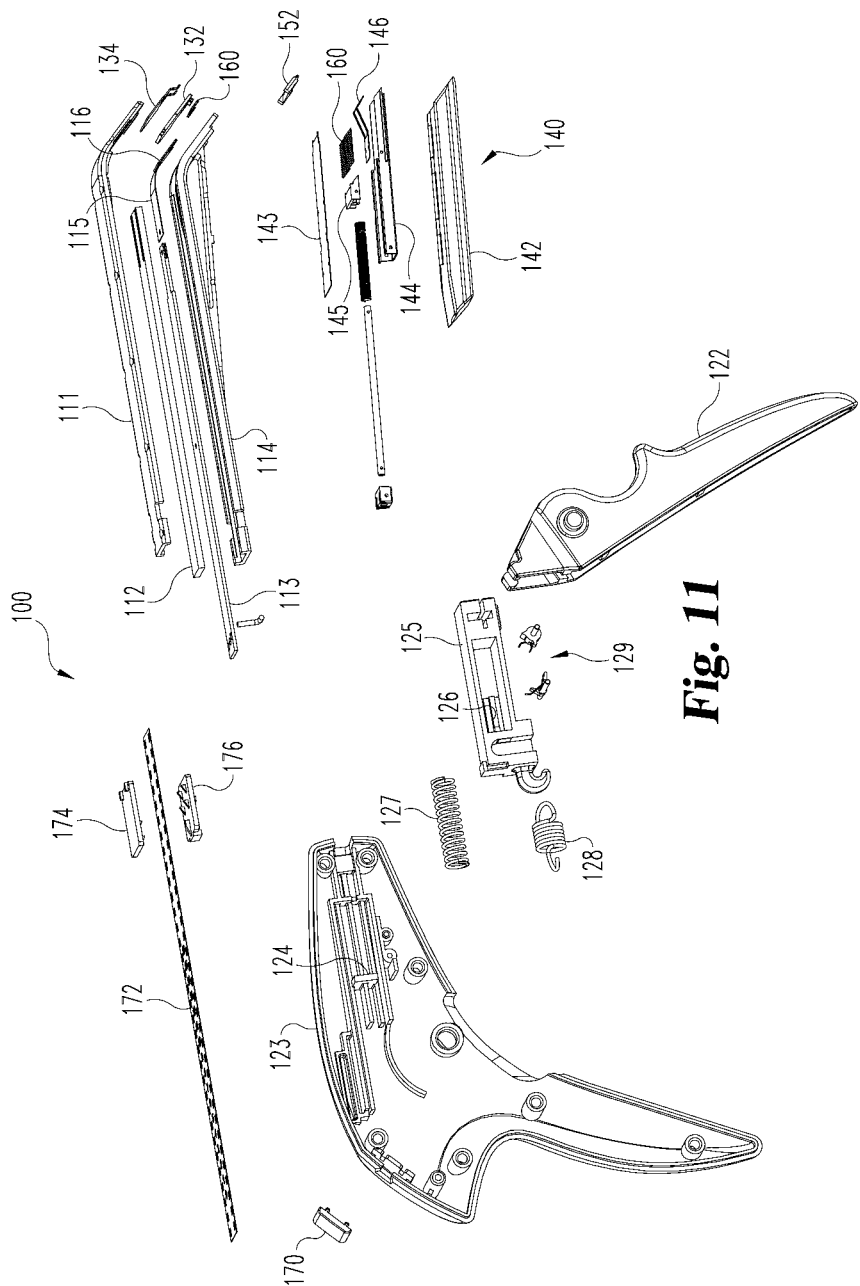
FIG. 11 is an exploded view of the FIG. 10 stapler with the second half of the handle omitted for clarity.

The total offset B between the bottom of the head and top of the shaft is preferably between 12 and 25 mm. Other angles and offset dimensions may be used if desired or necessary to the particular surgical site. The overall length between the head and the proximal end of tube 16 at its entrance to the handle 12 may be 85 mm, for example. Again, other dimensions may be determined according to the preference of the surgeon and the nature of the surgical site. The same is true as to the shape and nature of the handle, one example of a different shape is illustrated in FIGS. 10-11 as will be described. The width of the staple between the prongs may be 5 mm, for example, but staples of other widths might be selected for particular cases. For example, it may be desirable to produce a fully formed box staple using 0.5 mm staple wire wherein the formed staple has a width of about 7.5 mm and a height of about 3.5 mm. In some tools, it might be considered desirable to make the shaft rotatable in the handle and/or to provide an articulation joint in the shaft near where it enters the handle, but, for the present, it appears that simply inverting the handle from the attitude as shown in FIG. 1 to that as shown in FIGS. 7 and 9 would appear to be adequate. A variety of mechanisms for discharging a staple can be implemented. For example, U.S. Pat. Nos. 5,829,662 and 5,743,456 describe endoscopic stapling equipment that could be adapted to implement the present invention.

Referring now to FIGS. 10-14A, stapler 100 comprises a handle unit 120 and a downwardly disposed discharge head 130 at either end of an elongated shaft 110. A staple stack or magazine 140 containing a supply of staples (e.g. 15) is mounted to the underside of the shaft 110. Trigger 122 is operative to cause a staple 160 to be formed and discharged from an outlet port 162 of head 130. Successive pulls of the trigger form and discharge successive staples from the magazine 140, and a running staple count is displayed in a window at 170.

Formation and discharge of a staple is accomplished via a single stroke of pusher plate 116, which is coupled to trigger 122 via a mechanical linkage that extends through the shaft 110. More specifically, drive block 125 is mounted in a slot in housing 123 with one end of compression spring 127 over tab 126 and the other end against tab 124. The drive block 125 is coupled to a driver 113 or rigid bar, which is slidably disposed in the channel of shaft 110 defined between the upper cover 111 and base 114. A stiffener 112 is also provided in the shaft channel to increase structural rigidity of the elongated straight portion of the shaft 110. A flexible pusher 115 is coupled to the end of driver 113 and traverses the curved portion of the shaft channel, which includes support ribs for flexible pusher 115 in the upper cover 111 to reduce the possibility that the flexible pusher 115 would buckle or otherwise deform. Pusher plate 116 is laminated to the distal end of flexible pusher 115 for a seamless connection. Other connections are possible as well.

In operation, squeezing the trigger 122 drives block 125 to the right (FIGS. 10, 11), overcoming the restoring forces of springs 127, 128. Springs 127, 128 each function as a return spring, thereby providing redundancy, but their spring parameters may be selected to produce a desired effect (e.g. substantially increased return force at maximum trigger depression). As block 125 travels right, a one-way clutch assembly 129 engages cogs (not shown) on the underside of block 125 to prevent retraction of block 125 short of a full stroke. In addition, shuttle plate 176 is carried above block 125 and operates to advance numbered ribbon 172, which is sandwiched between shuttle plate 176 and stay plate 174 and provides a running count of staples via a window adjacent backing plate 170.

Figure 12:
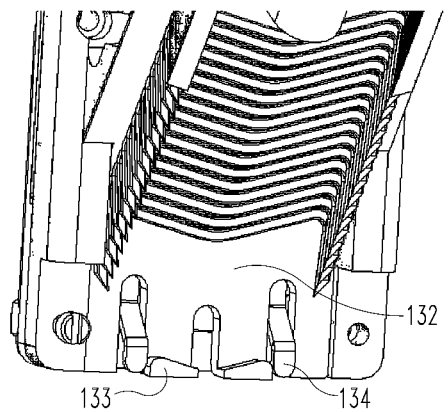
FIG. 12 is an underside view of the staple discharge head of the FIG. 10 stapler with the front wall piece 152 and the supporting magazine 140 for the staples removed for clarity.
Figure 13:
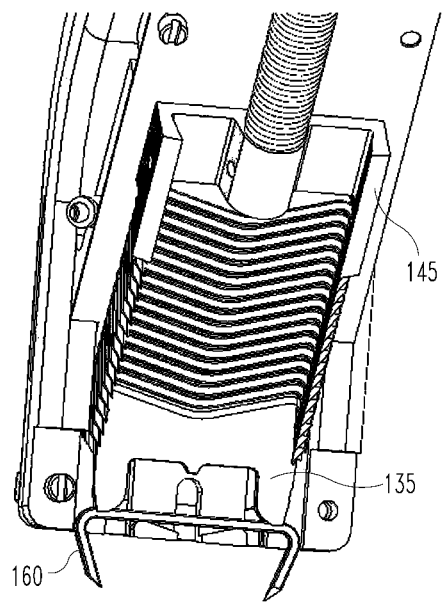
FIG. 13 is the underside view of FIG. 12 with a staple partially formed.

At the beginning of a stroke, pusher plate 116 is withdrawn into the discharge head 130, and the first staple in the magazine 140 is advanced into the firing breech. As shown in FIGS. 12 and 13, the staples in the magazine 140 are in the form of an angled stack, with each staple 160 in the stack oriented in its firing direction (i.e. parallel to the backwall 132 of the breech) and the axis of the stack 40-50 degrees from orthogonal to the firing direction.

As illustrated, the staples in the magazine are generally "M" shaped and are mounted over the front rails of a holder 144, with each hump over one of the rails. A cover plate 143 is secured to the top of holder 144 and a spring pusher 145 biases the staple stack 140 towards the open, angled end of the holder 144. As illustrated, the spring biasing pusher 145 has an uncompressed length greater than the length of the staple stack, which can serve to provide a more constant force on the staple stack as staples are discharged. Guide 146 is positioned at the open end of holder 144 and provides angled fingers that prevent the staples from dropping out the angled, open end prematurely. The staple magazine 140 is mounted to supporting rails on base 114 and covered by a protective shroud 142, and front wall piece 152 is secured to complete the assembly.

As it advances in its stroke, the forming fingers 135 of pusher plate 116 pick off the first staple from the stack and form the staple around anvil 133. FIG. 13 illustrates a partially formed staple extending from outlet port 162. Continuation of the forming fingers 135 serves to fully form the staple into a desired box like shape, and preferably with the staple prongs inverted slightly rearward. Retraction of forming fingers 135 releases the leaf springs 134, which had been displaced on the downstroke, which serves to displace the now-formed staple from anvil 133. Because the formed staple is narrower, it slips readily through the wider central opening of outlet port 162, as shown in FIGS. 14A-D.

Figure 14A:
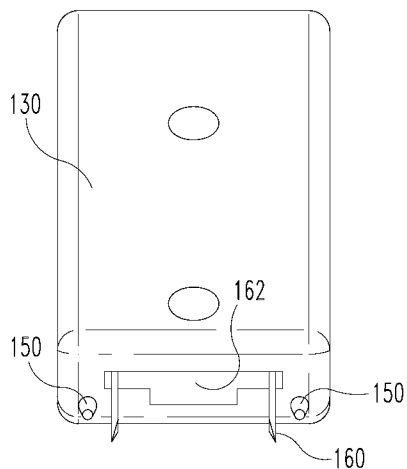
FIG. 14A is an end view of the discharge head of the FIG. 10 stapler, viewed in the direction of arrows 14-14 in FIG. 10.
Figure 14B:
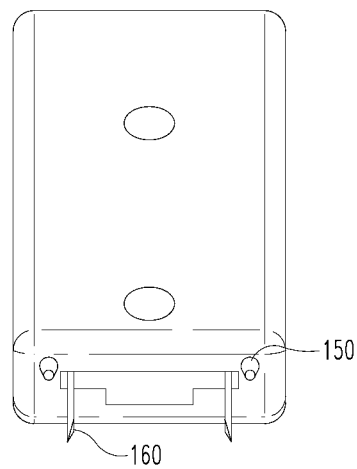
FIGS. 14B-D are views of alternative arrangements for the prongs on the discharge head.
Figure 14C:
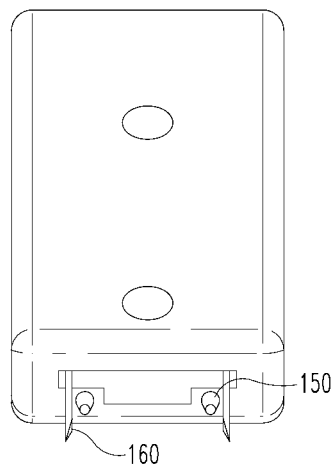
Figure 14D:
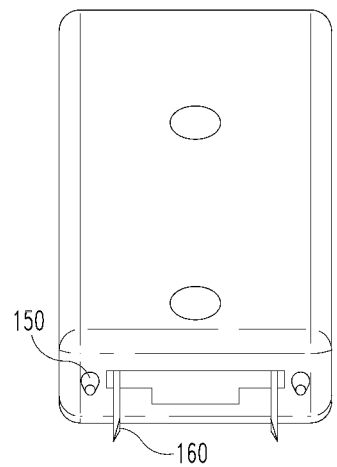

As illustrated, stapler 100 includes fixed prongs 150 on the underside outside of outlet port 162. Prongs 150 serve as mesh manipulators and may be used in any fashion contemplated herein. FIGS. 14B-D provide illustrations of additional or alternative locations for mesh manipulating prongs about the staple discharge port. Fixed prongs can also be used in combination with a retractable wire to provide further combinations of manipulating capabilities.

It is also contemplated that stapler 100 can be used without any means for mesh manipulation.

Numerous variations of the staplers described herein can be employed. For example, it may be desirable to provide one or more points of articulation along the shaft of the staplers described. As one example, a joint capable of 90 degrees articulation can be along shaft 110, for example near where shaft 110 and handle 120 meet. The provision of such an articulation joint may make it easier for the right handed surgeon, when operating on a right inguinal hernia, to place the staples that attach the mesh to the inguinal ligament.

Staples used herein can be absorbable or non absorbable with material inside the absorbable material for forming the staple and can be square shaped, round shaped, G shaped, etc. The staples can be stacked together along a rack inside the shaft that guides the staples to the distal end of the shaft with a spring loaded action, or a mechanism in the handle.

Procedures

Either under local anesthesia with sedation or general anesthesia, the lower abdomen is prepped and draped. A linear 6 to 8 cm skin incision is made along the natural skin lines. Hemostasis is obtained. The external oblique aponeurosis is divided, exposing the spermatic cord. Depending on what type of hernia, the hernia sac is dissected from adjacent tissues, emptied of any contents and pushed back into the peritoneal cavity. The mesh to be used is cut to its standard shape and size, and a tail slit is placed to accommodate the spermatic cord. The stapler is then used to fix the mesh to the insertion of the rectus sheath and along the inguinal ligament. More specifically, the stapler is used to fix the mesh to the rectus sheath, above its insertion to the pubic bone. (The stapler is sized and shaped to assure the safety of the femoral vessels and nerve.) The upper edge of the mesh is stapled to the rectus sheath and the internal oblique aponeurosis avoiding the iliohypogastric nerve. Either a staple or a single non-absorbable suture is then placed through the lower edges of the tails at the level of the internal ring. The wound is then closed in layers after all bleeding has been stopped and the sponge and instrument count is correct. The wound (i.e. the skin) can be closed with the stapler or with a conventional suture.

It is to be appreciated that what has been described includes an improved surgical stapler for attaching surgical mesh, comprising an elongated shaft having a handle at its proximal end and a downwardly disposed staple discharge port at its distal end, wherein the handle is operable to cause a supply of staples to be selectively discharged from the port; and one or more mesh manipulators near the port and projecting distal to the plane defined by the port.

What has also been described includes an apparatus for use by a person stapling mesh to body tissue at a site of inguinal hernia surgery and comprising: a handle for holding the apparatus adjacent the surgery site, and having a proximal end and a distal end; a shaft defining a longitudinal axis and having a proximal end and a distal end and having the proximal end mounted to the distal end of the handle; a staple discharge head having one end with a mounting portion connected to the distal end of the shaft, and having another end with a staple exit port; the head adapted to fire a staple out from said head through said port along a line and in a direction away from the handle, wherein the direction of staple firing is downward relative to the longitudinal axis of the shaft; an elongated member mounted to said shaft and extending generally parallel to the shaft and in a direction forward away from said handle, the member having a distal end portion in a plane containing the direction of staple firing, and the distal end portion of said member being spaced from said line and under the line; and the distal end portion of said member having a tip configured to engage a mesh useful for embedding in a body cavity during inguinal hernia surgery, for connecting and moving said mesh to a location for stapling the mesh to body tissue at the surgery site. In one refinement, the distal end portion of said member is straight and curves downward and then forward in said plane to said tip. In another refinement, the distal end portion of said member is straight and curves downward and then rearward in the plane to the tip. In another refinement, a guide on the shaft receives the elongated member and has a proximal end near the handle and a distal end opening exposing the distal end portion of the wire forward of the distal end opening of said guide, and confining the elongated member from the distal end portion of the member rearward to a location adjacent the handle. It may further include a manipulator on the elongated member adjacent the handle for alternately advancing and retracting the tip of the member.

What is also described is an apparatus for use in stapling mesh to body tissue at a site of inguinal hernia repair surgery and comprising: a shaft having a proximal end and a distal end; a staple discharging head at the distal end of the shaft; a staple inside the head, the staple having a generally U-shaped configuration with spaced prongs in a first plane; and a discharge port on the head for discharge of said staple outward from said head through the discharge port; and a mesh manipulator connected to the head and having a tip adjacent the port wherein the tip of the manipulator is spaced from said first plane a short distance to avoid contact by the staple when discharged outward from the port into the mesh.

What is also described includes, during inguinal hernia repair, a method of attaching a mesh covering herniated membrane, to body tissue adjacent and bordering the site of the herniation, and comprising: inserting the head of a stapling apparatus into an opening bordered by said tissue and directing a staple discharge port downward toward said mesh at a near side of said opening and firing staples from said port through said mesh into some of said tissue adjacent said herniation, at multiple locations on the near side of said opening; and moving the head of a stapling apparatus in an opening bordered by said tissue and directing a staple discharge port upward toward said mesh at a far side of said opening and firing staples from said port through said mesh into some of said tissue, at multiple locations on the far side of said opening. The method may further include engaging said mesh with a probe point mounted to said head and located between said port and said mesh, and moving said mesh with said probe to position said mesh at a location on said tissue where a staple is to be fired into said mesh and said tissue. The method may further include moving said mesh by pushing said mesh with said probe point and/or pulling said mesh with said probe point. Pulling the mesh may be used to lift said mesh on said far side. The mesh may be pierced to facilitate said moving of said mesh.

Figure 25:
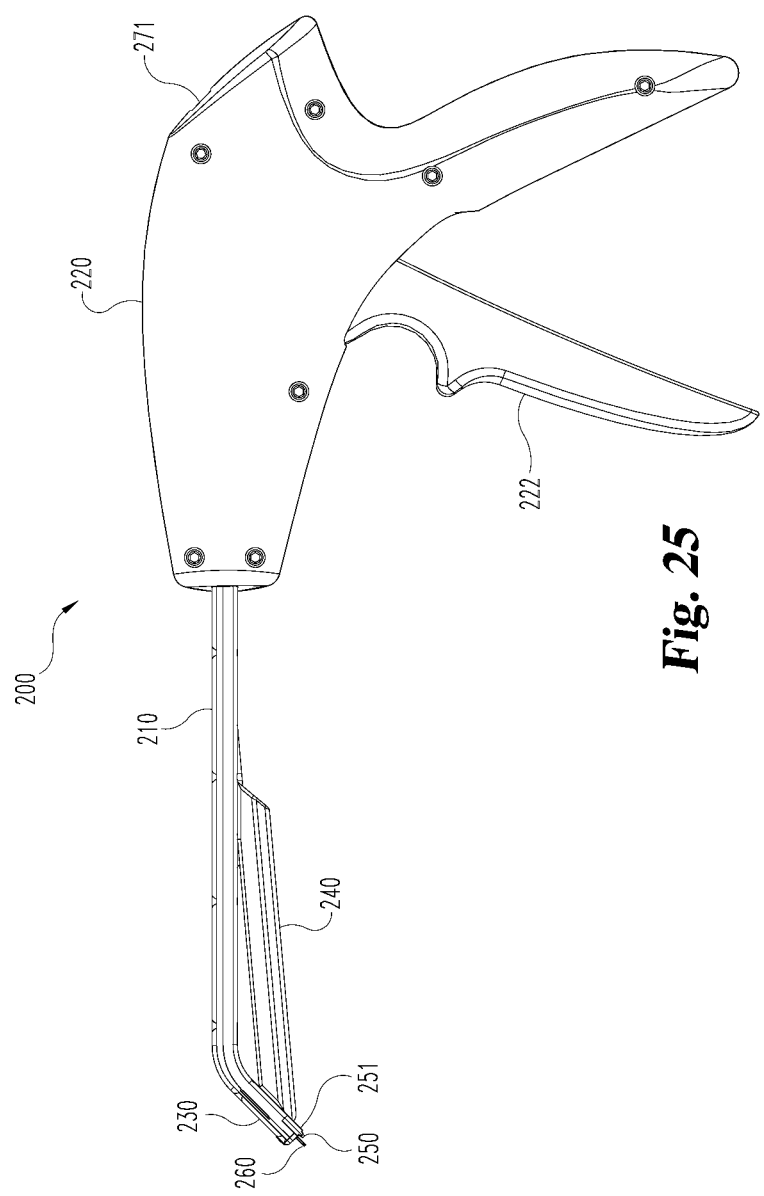
FIG. 25 is a side elevational view of another embodiment of a stapler.

Another embodiment of a stapler 200 is illustrated in FIGS. 15-27. It is to be appreciated, stapler 200 is similar to stapler 100 in many aspects; therefore, for the sake of brevity similar features will not be discussed. As illustrated in FIG. 25, stapler 200 includes a handle unit 220 and a downwardly disposed discharge head 230 at the distal end of an elongated shaft 210. A staple magazine 240 containing a supply of staples is mounted to the underside of the elongated shaft 210. Trigger 222 is operative to cause a staple 260 to be formed and discharged from an outlet port 251 of the discharge head 230. Successive pulls of the trigger 222 form and discharge successive staples from magazine 240, and a running staple count is displayed in a window 271. Stapler 200 also includes a pair of fixed prongs 250 near the outlet port 251. Prongs 250 are similar to prongs 150; therefore, prongs 250 serve as mesh manipulators and may be used in any fashion contemplated herein. It is also contemplated that stapler 200 can be used without any means for mesh manipulation, such as prongs 250.

Similar to stapler 100, formation and discharge of a staple is accomplished via a single stroke of a pusher plate 216, which is coupled to the trigger 222 via a mechanical linkage that extends through the elongated shaft 210. The mechanical linkage in the embodiment illustrated in FIGS. 15-27 is similar to the mechanical linkage described above and illustrated in FIGS. 10-14A. A flexible pusher 215 is coupled to the end of a driver (not shown) and traverses the curved portion of the channel of the elongated shaft 210. Pusher plate 216 is attached to the distal end of flexible pusher 215.

Figure 21:
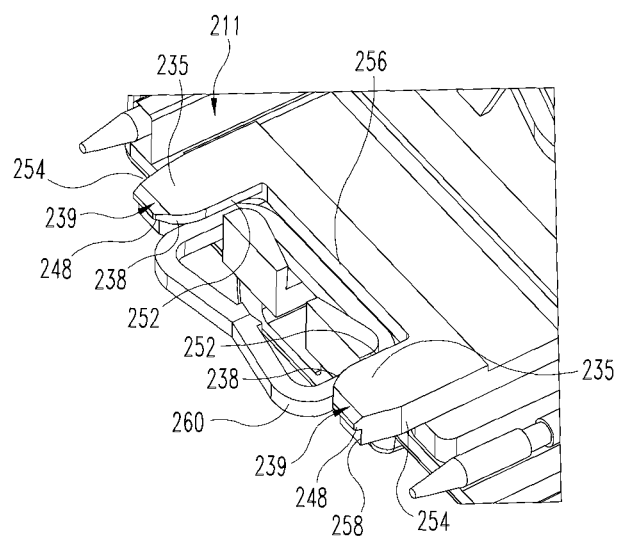
FIG. 21 is a partial view of the FIG. 20 embodiment.

Pusher plate 216 includes a pair of forming fingers 235 that are similar to forming fingers 135; however, each of forming fingers 235 as illustrated in FIG. 21 includes a chamfered portion 238, a cantilevered portion 248, and a retention lip 258. The chamfered portion 238, the cantilevered portion 248, and the retention lip 258 facilitate picking off a single staple 260 from the supply of staples. The chamfered portion 238 and cantilevered portion 248 pick off a single staple 260 as the pusher plate 216 passes under the stack of staples. As such, the chamfered portion 238 and cantilevered portion 248 do not engage the proximal staple surface to move another staple distally in the stack of staples. Therefore, the stack of staples remains undisturbed. In some applications, the use of fixed prongs 250 to hold mesh during a medical procedure may cause side loads or forces that are applied to the staple thereby resulting in tension on the staple and incomplete staple formation. These side loads or forces are out of the plane of the stapler 200 and can cause the staple to slip off the forming fingers 235. However, the cantilevered portion 248 and the retention lip 258 retain the staple between forming fingers 235. The retention lip 258 engages the top of the staple 260 during formation of the staple 260 to restrain the staple 260 from forces caused by prongs 250 on the mesh as the staple 260 is attached to body tissue. The cantilevered portion 248 helps to retain the staple 260 from slipping or twisting away from the retention lip 258. Each of the forming fingers 235 includes an inner edge 252, an outer edge 254, and a staple contact portion 239 that spans between the inner edge 252 and the outer edge 254. The inner edge 252 includes the chamfered portion 238. The inner edge 252 and the staple contact portion 239 include the cantilevered portion 248 and the retention lip 258. Between the pair of forming fingers 235 is positioned a wider portion 256 that is substantially perpendicular to the inner edge 252.

The channel of the elongated shaft 210 is defined between an upper cover 211 and a base 214. The base 214 includes a first key or tab 300 positioned on a first edge 302 and a second key or tab 304 positioned on a second edge 306 as illustrated in FIGS. 22, 23, and 24. The base 214 also defines a first opening 308 adjacent the first key 300 on the first edge 302. The base 214 also defines a second opening 309 adjacent the second key 304 along the second edge 306. The first key 300 and the second key 304 are sized and configured to interact and engage a first keyway 310 and a second keyway 312, respectively, on a backwall or anvil plate 232. Further, the first opening 308 is sized to receive the first keyway 310. Correspondingly, the second opening 309 is sized to receive the second keyway 312. As the backwall 232 is assembled with the base 214, the first keyway 310 is positioned and inserted in the first opening 308 and the second keyway 312 is positioned and inserted in the second opening 309 as illustrated in FIG. 23. Thereafter, the backwall 232 is slid or pushed toward the distal end of the elongated shaft 210 to engage the first keyway 310 with the first key 300 and the second keyway 312 with the second key 304. The first key 300 engages and retains the first keyway 310 and the second key 304 engages and retains the second keyway 312. The connection between the first key 300 and the first keyway 310 and the connection between the second key 304 and the second keyway 312 provides a mechanical interaction between the backwall 232 and the base 214. As such, adhesive is not required to attach the backwall 232 with the base 214. In other embodiments, adhesive may be used, if desired, to attach the backwall 232 with the base 214.

Figure 15:
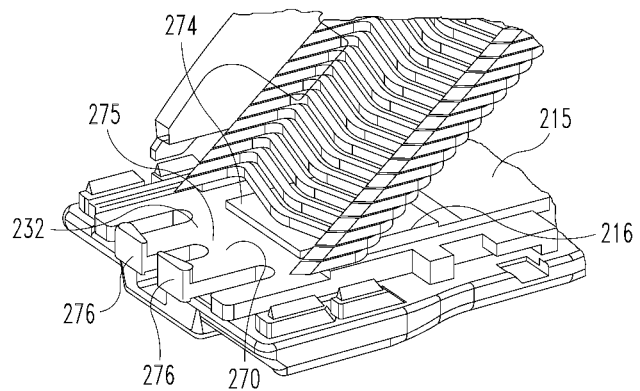
FIG. 15 is an underside view of another embodiment of a staple discharge head with a front wall piece and a supporting magazine for staples removed for clarity in an initial position.
Figure 16:
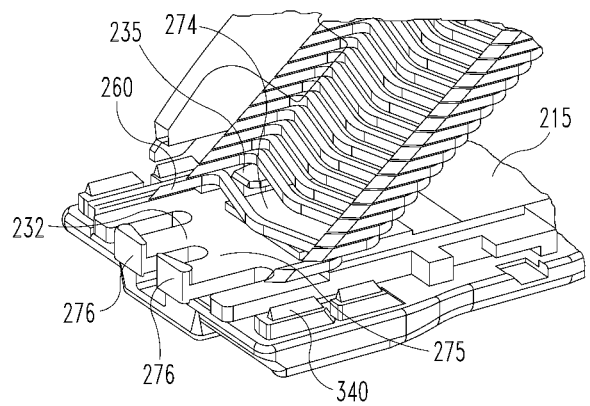
FIG. 16 is the underside view of the FIG. 15 embodiment with one staple stripped from a stack of staples wherein the single staple is resting on a step on a back wall plate.

The backwall or anvil plate 232 includes a top face 272 and an opposite bottom face 270. The top face 272 is positioned to face or interact with the supply of staples when the backwall 232 is assembled with the base 214 of elongated shaft 210. The top face 272 includes a step or plateau 274 that has a thickness that corresponds to about the thickness (or less) of a single staple. The step 274 functions as an elevated staple staging area for the supply of staples. The width of step 274 is about the same as wider portion 256 of pusher plate 216. As such, the forming fingers 235 of pusher plate 216 slide next to the step 274 as the chamfered portion 238, the cantilevered portion 248, and the retention lip 258 pick off a single staple and advance that staple toward a pair of anvils 276 as described in more detail below. The top face 272 also includes a lower portion 275 that is positioned between the step 274 and a pair of anvils 276. Similar to backwall 132, backwall 232 includes a pair of anvils 276 around which the staple 260 is formed. The uppermost staple from the supply of staples rests against the step 274 such that a center portion of the staple contacts the step 274 while the outer legs of the staple rest against lower portion 275 thereby causing the staple to rotate slightly. As such, the center portion of the staple is elevated above the legs of the staple as shown in FIG. 15. As the staple is pushed by the forming fingers 235, the staple passes over the step 274 and drops onto the lower portion 275 such that the staple is retained in the retention lip 258. The remainder of the pusher plate 216 passes over the step 274 as the staple engages the anvils 276. Moreover, the step 274 and pusher plate 216 each have a thickness that enables the chamfered portion 238 to pass under a second staple in the stack of staples (as shown in FIGS. 15 and 16) and engage only the staple resting on step 274 to ensure pickoff of only one staple.

The staple contact portion 239 is beveled to further facilitate the forming fingers 235 engagement of a single staple. The staple contact portion 239 does not disturb the adjacent staple and helps to eliminate staple jamming. The chamfered portion 238, staple contact portion 239, cantilevered portion 248, and retention lip 258 on pusher plate 216 and the step 274 on backwall 232 work together to ensure that only a single staple 260 from the supply of staples is ejected at deployment.

Figure 26:
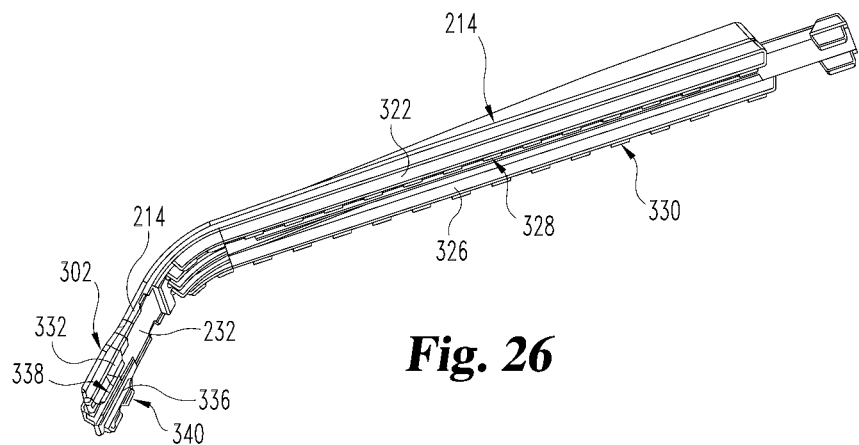
FIG. 26 is a side elevational view of an elongated shaft of the FIG. 25 embodiment.
Figure 27:
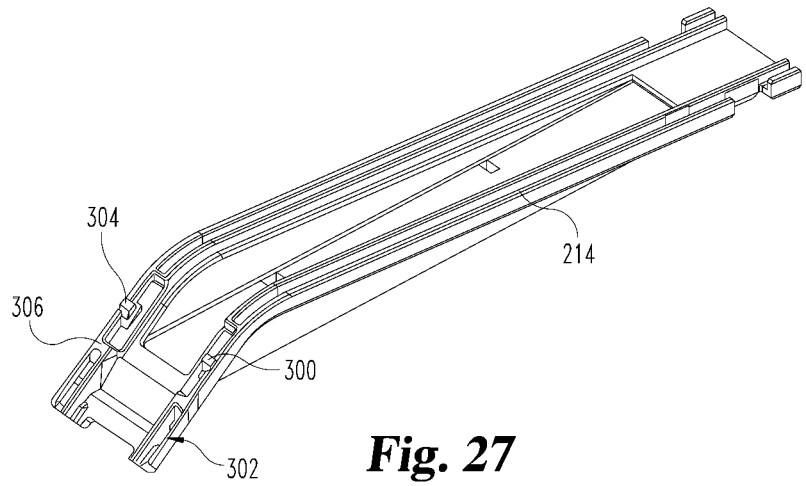
FIG. 27 is a top elevational view of the FIG. 26 embodiment.

The base 214 also includes a first rail 322 and an opposite second rail 326 as shown in FIGS. 26 and 27. In the illustrated embodiment, the first rail 322 includes a first plurality of energy directors 328 and the second rail 326 includes a second plurality of energy directors 330. The first and second plurality of energy directors 328 and 330 each have a wedge or rectangular shape; however, the energy directors 328 and 330 can be shaped differently in other embodiments. The base 214 also includes a first distal rail 332 along the first edge 302. The base 214 also includes a second distal rail 336 along the second edge 306. The first and second distal rails 332 and 336 include a first plurality of energy directors 338 and a second plurality of energy directors 340, respectively. To join the base 214 with the staple magazine 240, a cover plate (not illustrated) of the staple magazine 240 is positioned next to the base 214. Next, ultrasonic welding equipment is used to provide ultrasonic energy to melt the plurality of energy directors 328, 330, 338, and 340 to create a joint between the base 214 and the cover plate. Other embodiments may use different techniques to attach the staple magazine 240 to the base 214. Some examples include adhesive, snap-fit connections, or other mechanical type connections.

Figure 17:
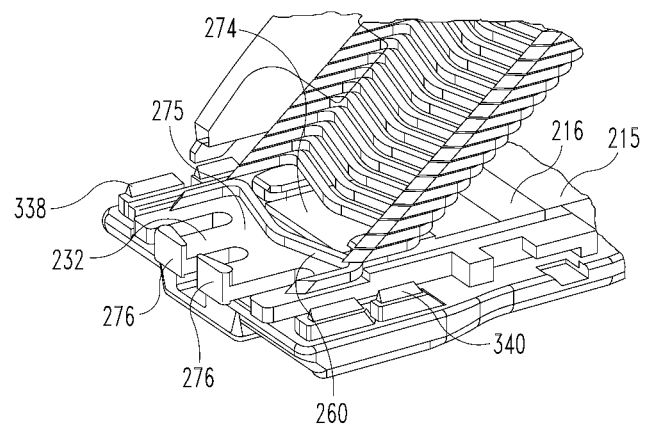
FIG. 17 is the underside view of the FIG. 15 embodiment with the single staple adjacent the step on the back wall plate.
Figure 18:
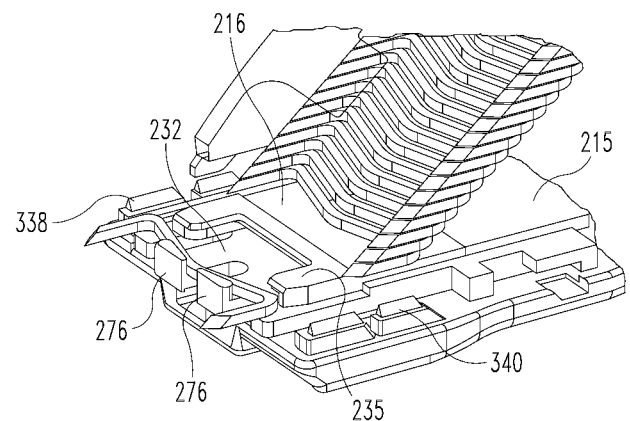
FIG. 18 is the underside view of the FIG. 15 embodiment with the single staple in contact with the anvils.
Figure 19:
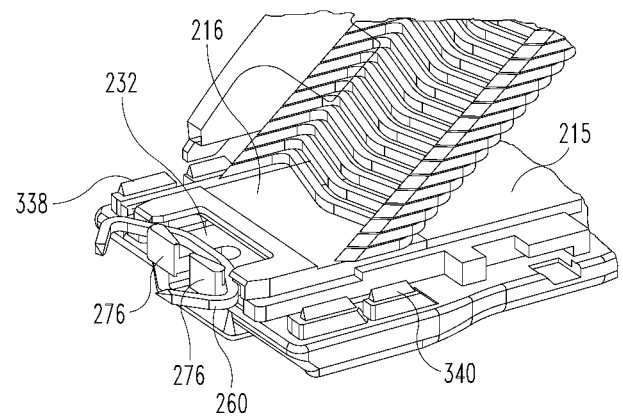
FIG. 19 is the underside view of the FIG. 15 embodiment with the single staple partially deformed around the anvils.
Figure 20:
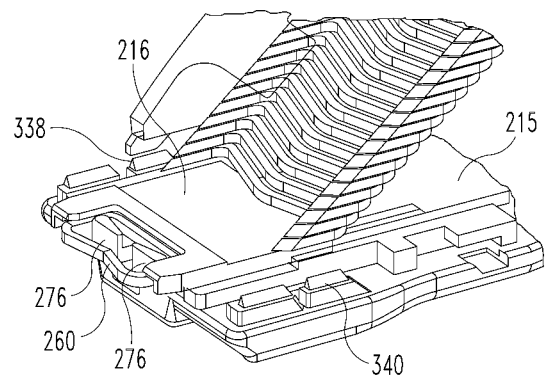
FIG. 20 is the underside view of the FIG. 15 embodiment with the single staple fully formed around the anvils.

In operation, the trigger 222 is squeezed which drives the block (not illustrated but similar to block 125) to the left in FIG. 25. At the beginning of a stroke, pusher plate 216 is withdrawn into the discharge head 230, and the first staple in the magazine 240 is advanced into the firing breech. The staples in magazine 240 are similar to the staples in magazine 140. As pusher plate 216 advances in its stroke, the forming fingers 235 contact and pick off the first staple from the stack as illustrated in FIG. 16. In particular, the cantilevered portion 248 on the staple contact portion 239 engages the staple 260 and pushes the staple 260 towards the pair of anvils 276 as the pusher plate 216 continues to advance. Also, the cantilevered portion 248 on the staple contact portion 239 and the chamfered portion 238 of the pusher plate 216 clear or pass under the staple that is adjacent to staple 260 in the stack of staples. As such, the remaining staples are generally undisturbed during deployment. Next, as the pusher plate 216 advances forward, the staple 260 moves off the step 274 and onto the lower portion 275 such that the retention lip 258 engages the top of the staple 260 as illustrated in FIG. 17. As the pusher plate 216 continues to advance forward, the staple 260 contacts the pair of anvils 276 as illustrated in FIG. 18. Thereafter, as illustrated in FIG. 19, chamfered portion 238 and retention lip 258 continue to engage and retain the staple 260 adjacent the pair of anvils 276 and fully form the staple 260 into a desired box like shape, and preferably with the staple prongs inverted slightly rearward as illustrated in FIG. 20. Therefore, if force is applied to the staple 260, the cantilevered portion 248 assists to retain the staple 260 on the retention lip 258. Retraction of the pusher plate 216 releases leaf springs (not illustrated) which had been displaced on the down stroke, which serves to displace the now-formed staple 260 from the pair of anvils 276.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. A surgical stapler, comprising:
   an elongated shaft having a handle at its proximal end;
   a discharge head fixedly attached to a distal end of the elongated shaft, the discharge head disposed at an acute angle relative to the longitudinal axis of the elongated shaft;
   a magazine of staples mounted between the discharge head and the shaft, the magazine of staples oriented at an acute angle relative to the longitudinal axis of the elongated shaft; and
   a pusher plate disposed in the discharge head, the pusher plate including a pair of forming fingers adapted to retain a single outermost staple from the magazine of staples between the forming fingers; and
   an anvil plate positioned in the discharge head adjacent the pusher plate, the anvil plate having a step with a height of about a thickness of the single staple, wherein the single staple is positioned against the step such that a center portion of the single staple contacts the step and outer legs of the single staple rest against a lower distal portion of the anvil plate wherein the distal portion is relative to the step of the anvil plate to cause the single staple to rotate away from the magazine of staples.

2. The surgical stapler of claim 1 wherein each of the pair of forming fingers includes a retention lip.

3. The surgical stapler of claim 2 wherein the retention lip has a height of about a thickness of the single staple.

4. The surgical stapler of claim 1 wherein each of the pair of forming fingers includes an inner edge, an outer edge, and a staple contact portion that spans between the inner and outer edges, wherein the inner edge and the staple contact portion include a retention lip.

5. The surgical stapler of claim 1 wherein each of the pair of forming fingers includes a chamfered portion adapted to engage only the single staple from the magazine of staples.

6. The surgical stapler of claim 5 further comprising an anvil plate positioned in the discharge head adjacent the pusher plate, the anvil plate having a step with a height of about the thickness of the single staple, the step is adapted to position the single staple under the chamfered portion when the pusher plate passes over the anvil plate.

7. The surgical stapler of claim 6 wherein the pair of forming fingers are adapted to slide adjacent the step.

8. A surgical stapler, comprising:
   an elongated shaft having a handle at its proximal end and a staple discharge head fixedly attached at its distal end, the staple discharge head disposed at an angle between 30 degrees and 50 degrees relative to the longitudinal axis of the elongated shaft, wherein the handle is operable to cause a single staple from a magazine of staples to be selectively discharged from the head;
   a pusher plate positioned in the staple discharge head, the pusher plate including a retention lip adapted to retain the single staple from the magazine of staples, wherein the pusher plate includes a chamfered portion adapted to engage only the single staple from the magazine of staples; and
   an anvil plate positioned in the discharge head adjacent the pusher plate, the anvil plate having a step with a height of about the thickness of the single staple, the step is adapted to position the single staple under the chamfered portion when the pusher plate passes over the anvil plate.

9. The surgical stapler of claim 8, wherein the pusher plate includes a cantilevered portion adapted to engage and remove the single staple from the magazine of staples.

10. The surgical stapler of claim 8, wherein the elongated shaft includes a first tab and a second tab, the anvil plate defines a first keyway and a second keyway, the first and second tabs are adapted to engage and retain the first and second keyways, respectively, when the anvil plate is assembled with the elongated shaft.

11. The surgical stapler of claim 8, wherein the pusher plate includes a pair of forming fingers adapted to retain a single staple from the magazine of staples between the forming fingers.

12. A surgical stapler, comprising:
   an elongated shaft having a handle at its proximal end and a staple discharge head at its distal end, the staple discharge head disposed at an acute angle relative to the longitudinal axis of the elongated shaft, wherein the handle is operable to cause a single staple from a magazine of staples to be selectively discharged from the head;
   an anvil plate positioned in the staple discharge head, the anvil plate having a step with a height of about the thickness of a single staple, the step located adjacent the magazine of staples such that a center portion of the single staple from the magazine of staples rests on the step and a pair of outer legs of the single staple rest against a lower distal portion of the anvil plate wherein the distal portion is relative to the step of the anvil plate to rotate the single staple away from the magazine of staples; and a pusher plate positioned in the staple discharge head, the pusher plate having a pair of forming fingers with a distance between the pair of forming fingers that is greater than a width of the step such that the forming fingers slide adjacent the step to remove the rotated single staple from the magazine of staples.

13. The surgical stapler of claim 12 wherein the pusher plate includes a retention lip adapted to retain the single staple from the magazine of staples during a hernia surgery.

14. The surgical stapler of claim 1 wherein the discharge head disposed at the acute angle relative to the longitudinal axis of the elongated shaft is between 30 degrees and 60 degrees; and the magazine of staples oriented at the acute angle relative to the longitudinal axis of the elongated shaft is between 30 degrees and 60 degrees.

15. The surgical stapler of claim 12 wherein the staple discharge head disposed at the acute angle relative to the longitudinal axis of the elongated shaft is between 30 degrees and 60 degrees.

\* \* \* \* \*